United States Patent [19]
Lemelson

[11] Patent Number: 5,946,220
[45] Date of Patent: *Aug. 31, 1999

[54] COMPUTER OPERATED MATERIAL PROCESSING SYSTEMS AND METHOD

[76] Inventor: Jerome H. Lemelson, Suite 286, Unit 802 930 Tahoe Blvd., Incline Village, Nev. 89451

[ * ] Notice: This patent is subject to a terminal disclaimer.

[21] Appl. No.: 08/658,317

[22] Filed: Jun. 5, 1996

Related U.S. Application Data

[63] Continuation-in-part of application No. 08/174,183, Dec. 27, 1993, Pat. No. 5,525,240, application No. 08/252,250, Jun. 1, 1994, abandoned, and application No. 08/111,638, Aug. 25, 1993, abandoned.

[51] Int. Cl.⁶ .................................................. G01N 15/06
[52] U.S. Cl. .................... 364/528.08; 73/61.48; 210/745; 210/787; 436/45
[58] Field of Search ........................................ 364/502, 500, 364/496, 555, 528.08, 528.39, 528.01; 73/1.87, 61.43, 61.44, 61.48, 64.56; 422/72, 74; 436/45, 43, 50; 356/39, 426, 427, 335, 336, 338; 210/745, 600, 739, 767, 781, 787, 143, 512.1; 435/286.5; 494/1, 7, 9, 10, 37

[56] References Cited

U.S. PATENT DOCUMENTS

| | | | |
|---|---|---|---|
| 4,671,102 | 6/1987 | Vinegar et al. | 73/61.48 |
| 4,736,311 | 4/1988 | Takeuchi et al. | 364/555 |
| 5,240,856 | 8/1993 | Goffe et al. | 435/286.5 |
| 5,308,506 | 5/1994 | McEwen et al. | 210/745 |
| 5,449,621 | 9/1995 | Klein | 436/45 |
| 5,525,240 | 6/1996 | Lemelson | 210/745 |

*Primary Examiner*—Melanie A. Kemper
*Attorney, Agent, or Firm*—Niro, Scavone, Haller & Niro

[57] ABSTRACT

Improvements in computer controlled material processing are disclosed including an apparatus and method in which the centrifugation of a liquid mixture in order to separate out components of the mixture with different sedimentation rates is adaptively controlled by monitoring the sedimentation of detectable particles and controlling the centrifugation so as to effect a desired localization of the detectable particles. Such adaptive control may be performed with a continuous flow centrifugal separator or a batch-type centrifuge. The detectable particles may be test particles having a sedimentation constant approximately equal to a component of interest in the mixture whose localization is desired.

8 Claims, 7 Drawing Sheets

COMPUTER OPERATED MATERIAL PROCESSING SYSTEMS AND METHOD

This application is a continuation-in-part of Ser. No. 08/174,183 filed Dec. 27, 1993 now U.S. Pat. No. 5,525,240; Ser. No. 08/252,250 filed Jun. 1, 1994 now abandoned; and Ser. No. 08/111,638 filed Aug. 25, 1993, now abandoned.

BACKGROUND AND SUMMARY OF THE INVENTION

The present invention relates to improvements in methods and systems for controlling material processing operations such as mixing, separation, maintenance, and material analysis. Such improvements are applicable to industrial plants such as chemical plants, power plants, oil refineries as well as to specialized material processing or analysis equipment such as chemical analyzers.

A common method for separating out heavier components from a liquid mixture is the use of centrifugation, whereby the mixture is subjected to a centrifugal force field which causes the sedimentation of the components at different rates according to their densities and volumes. In a centrifuge for separating biological cells, for example, a suspension of cells in a liquid medium is placed in a centrifuge tube which is rotated rapidly about an axis some distance from the tube so as to cause sedimentation of the cells and other structures toward the bottom of the tube. Cells or other particles may thus be separated differentially by varying the time of centrifugation with the denser components settling at the bottom of the tube first. Such differential centrifugation is commonly used, for example, to separate red blood cells from white blood cells owing to the greater density of the former. After disruption of cells into a heterogeneous liquid, centrifugation is also used to separate cellular constituent parts such as nuclei, mitochondria, ribosomes, etc.

Any heterogeneous liquid mixture may be subjected to centrifugation. A more clearly demarcated degree of separation may be achieved, however, by interposing a density barrier which only particles having a greater density may penetrate. For example, a blood cell suspension may be layered over a solution of albumin or sucrose whose density is between that of red and white cells, allowing the red cells but not the white cells to go through the density barrier which affords a better separation. Modifications of this technique, called density gradient centrifugation, include using a centrifuge medium having a number of layers of varying density or using a medium having a continuous density gradient along the length of the centrifuge tube. If the different densities of the medium encompass the range of densities represented by the different components desired to be separated, each component will come to rest in a layer of the medium whose density matches its own.

Centrifugation may also be used in a continuous flow process in which heavier or lighter components are removed from a feedstock. Centrifugal separators of this type are commonly used in the dairy and paper industries as well as in isotopic separation processes. Since the liquid which is centrifuged in these cases is the feedstock itself and not a special centrifugation medium, it is usually not possible to employ the density gradient technique as described above to enhance the degree of separation of the components. A cleaner separation may be achieved, however, by the use of multi-stage centrifugal separators in which the feedstock is continuously depleted of either the heavier or lighter components as it proceeds through the multiple stages.

In any of the centrifugal separation processes described above, it would be advantageous if the centrifuge could be operated so as to optimize the separation of a select component or components from the rest of the mixture. For example, in density gradient centrifugation, the centrifugation must proceed long enough for the different particles to localize in their individual density layers. How long this takes depends on the sedimentation constants of the particles, the rotational speed of the centrifuge, and the composition of the centrifuge medium. If the centrifugation is allowed to proceed for too long and at too high a speed, however, disruption of the desired layers as well as fragile components such as cells may occur. In accordance with the present invention, therefore, a quantity of detectable test particles having a sedimentation constant approximately equal to that of a select component of a mixture which it is desired to separate is added to the mixture before or during the centrifugation. Such test particles, depending upon the type of mixture component whose sedimentation rate they are designed to emulate, may be either molecules or larger particles to which is conjugated a tag enabling the test particle to be detected by electro-optical or other means. The position and/or velocity of the test particles in the mixture as centrifugation proceeds is monitored by a scanning device which feeds the position data to a computer which then controls the speed and duration of the centrifuge so as to result in a desired localization of the component which it is desired to separate. By means of such adaptive control of the centrifuge, its operation may be optimized to separate out a select component even as the composition of the centrifuge medium varies. The technique is thus especially useful in those applications where centrifugation takes place in a native medium subject to a great deal of variability as opposed to an artificial centrifuge medium.

The present invention may also be used in continuous centrifugal separation operations to control the speed of each of the individual centrifugal separation stages so as to result in the optimum separation of a select component or components from the feedstock. Other variables which may also be controlled include impeller blade angles and rate of throughput into each stage. In a continuous separation operation, test particles are continuously added to the feedstock, and the concentration of the particles is continuously monitored in the product coming out of the separator. A plurality of different test particles may also be used with each having a sedimentation constant corresponding to a different component of the feedstock. Select components may then be optimally stripped from the feedstock by removing product from select stages and operating the stages in accordance with the concentration of test particles in each product stream. In cases where it is desired to remove the test particles from the product, the particles may be composed or partly composed of a ligand having a binding affinity for specific molecules immobilized in a reaction column. The test particles may then be separated from the rest of the product by passing the product through the reaction column.

Mixing is a common operation that effects the distribution, intermingling, and homogeneity of matter and is almost always accomplished by agitation of the matter components to be mixed. Other processes, such as chemical reaction, mass transfer (including solubility and crystallization), heat transfer, and dispersion, are also promoted by agitation. The type, extent, and intensity of agitation determine both the rates and adequacy of a particular process result. Agitation may be performed by different types of equipment, but most liquid mixing is done by rotating impellers in cylindrical vessels. A typical impeller-type liquid mixer includes a vessel, an impeller and a plurality of side mounted baffles. The forces applied by the impeller develop circulation or bulk flow within the matter to be mixed. Superimposed on this flow pattern is molecular diffusion, and if turbulence is present, turbulent eddies, both of which provide intermingling of the component particles at a micro level.

Bulk circulation results when the fluid stream is discharged by the impeller, while turbulence is generated mostly by the velocity discontinuities adjacent to the stream of fluid flowing from the impeller. Turbulence spreads throughout the bulk flow and, although attenuated, is carried to all parts of the vessel. It is recognized that some mixing operations require relatively large bulk flows, whereas others need a high degree of turbulence. It follows therefore that there is an optimum ratio of flow to turbulence for any particular mixing operation. Kinetic energy imparted to the fluid by the mixing impeller produces both bulk flow and turbulence, with a high rotational speed tending to produce more turbulence and a large diameter tending to produce more bulk flow. Impeller shape also has an effect which can be significant, with a rotating disk representing the extreme case for producing high turbulence. The ratio of bulk flow to turbulence also depends on the shape of the mixing vessel; the fittings it contains; the type, size, and position of the impeller; and, of course, the properties of the fluid. Radial and vertical flow currents penetrating to all portions of the fluid usually produce the best mixing. Vertical baffles are commonly provided to effect such flow patterns for impellers which are centrally located, while they may be omitted if an impeller used in an off-center position.

Mixing impellers may be of several types (such as a marine-type propeller, a pitched-blade turbine, or a flat paddle wheel), but any of them centrally positioned produce rotating fluid motion with a vortex around which liquid swirls. This motion constitutes bulk flow but often results in separation or stratification rather than intermingling. The result is little turbulence and only a small amount of vertical and lateral flow motion. Inserting projections into the body of the fluid (ie., baffles) stops the rotary motion, and the vortex disappears, thus improving the mixing. FIG. 2 shows the the desireable vertical and lateral flow patterns produced by a centrally located impeller in a mixing vessel having baffles from the side and bottom, respectively.

It is possible, of course, to design a mixing apparatus for a particular process involving the mixing of particular components under specified conditions that produces an optimal ratio of turbulence to bulk flow. It would be desirable, however, if a mixing apparatus could be provided which is capable of adapting to different process conditions (such as different material components) by dynamically adjusting mixing variables in a manner which optimizes the mixing.

One aspect of the present invention relates to a system and method for mixing fluent materials, such as solid or liquid particles, liquids, viscous solids or liquids, or combinations thereof, under the control of a computer. In particular, the invention involves sensing and scanning techniques for scanning materials as they are mixed and generating feedback signals which are computer processed and analyzed to generate control signals wherein such control signals are employed to control and vary accordingly one or more mixing process variables to optimize and/or enhance the mixing operation. In one particular form of the invention, a machine vision system or systems are employed to electro-optically detect such variables as the colors or densities of two or more materials being mixed, the shape or shapes of solid or liquid particles at one or more time during the mixing operation, and/or flow patterns occurring within the mixing vessel. Such optical variables may be detected and quantized by employing one or more television cameras, photoelectric scanning systems, and/or radiation generated by one or more lasers.

In one form of the invention, a single television camera is positioned to scan the surface of mixing materials during the mixing operation and the resulting video signals are computer processed and analyzed by comparing the results of processing with image information, such as codes, derived from memory. The mixing operation may be terminated by signals generated by the computer when it electronically recognizes that the mixed material has a color, shade or variations thereof which indicate, by signal comparison or other means, that mixing is complete.

In another form, a laser beam is caused to intersect while directed without scanning, a select portion of the surface of the mixing material and/or to scan same in a select path whereupon the reflected light of the laser beam and/or spectral light energy generated by one or more of the mixing materials, is photoelectrically detected by one or more photoelectric cells and/or by solid state detection elements or a television camera. The scanning and detection process continues during the mixing operation and the resulting image signals are computer processed and analyzed in a manner to detect when mixing is complete and, in certain instances, when mixing is taking place incorrectly. The resulting coded electrical signals are employed to control and/or terminate the mixing operation. Such control may be effected in a number of ways including controlling one or more motors rotating one or more mixing assemblies, such as blades, turbines or other mixing devices; control of one or more valves and/or motors which pump or otherwise affect the flow of one or more of the fluent materials being mixed; control of radiation applied to the mixing materials; control of one or more ultrasonic energy generating transducers employed in mixing; control of pressure in the mixing chamber, or control of other process variables affecting the mixing process. Fuzzy logic and neural networks electronic hardware and software may be employed in the computer analysis of the image information derived from scanning the surface or surfaces of the mixing materials and, in certain instances, from image information derived from one or more electro-optical scanners scanning reflections of laser light within the mixing fluids wherein such electro-optical scanners are disposed within one or more tubes extending into the mixing materials and/or supported by the mixing blades or a portion of the mixer assembly.

Another aspect of the invention relates to a system and method for performing experiments and diagnostic tests, such as relating to chemistry, medicine and other areas of technology involving systematic procedures and steps which may be computer controlled and wherein results of the experiments or analyses may be electronically detected, processed and analyzed. In particular, the invention is concerned with such an experimentation or test system and method wherein a computer is utilized to control experiments and tests, determine and analyze results, and make decisions with respect to additional or future experiments and tests without the need for human attendance, analysis or decision-making. In one form, a digital computer is programmed to receive and analyze data generated by sensors which sense and detect variations in matter, such a chemicals or living tissue, as an experiment progresses and which analyze and generate electrical signals indicative of the results of the experiment. Such electrical signals are compared with signals generated from recordings in a memory and are processed therewith to generate additional control signals for effecting either continuation of the experiment or the performance of an additional experiment or experiments with respect to the chemicals or living matter which has been generated or affected by the prior experiment. This process is repeated a number of times, either until a desired result has been obtained or a number of steps has been effected wherein a previously unknown result has occurred and may be indicated by sensing such result. In a particular form, the system includes supplies of a variety of different materials and means for controllably dispensing or carrying such materials to selective locations within the system and/or to or within a specimen being subjected to test of experimentation. By utilizing such a system and method involving the computer control of one or more simultaneously and/or consecutively conducted experiments with computer analysis of results to determine future experiments to be performed, experimental procedure may be substantially improved by eliminating unnecessary testing and reducing the time required to perform one or a series of experiments.

Another aspect of the present invention relates to an apparatus and method for automatically inspecting, maintaining, repairing, assembling and/or cleaning containers such as large storage tanks. Storage devices, such as large cylindrical tanks, are employed in many industries including the chemical, drug and biological industries to store a variety of fluent materials and solids contained in liquids, and, in certain instances, to permit the processing of matter within the tanks, wherein contamination may periodically take place requiring that the tanks be emptied or reduced in contents and cleaned. Heretofore, such tanks must be emptied and taken out of service before any cleaning, repairing, or inspecting of the tank's inner walls can be undertaken. The cleaning operation is generally performed by one or more human beings with brushes, hoses and nozzles for cleaning liquids steam and the like, operable to remove contaminants from the inside surfaces of the side walls and bottoms of the tanks.

In accordance with the invention, disposed within a tank is an automatic manipulator having one or more operating heads for containing one or more devices such as spray nozzles, brushes, and inspection or handling devices. The operating head(s) is attached to a manipulator arm which extends laterally from a rotor assembly so that the operating head engages an inner wall surface of the tank. The rotor assembly is disposed so as to be rotatable about a central axis of the tank, and the manipulator arm is mounted to the rotor assembly so as to be vertically adjustable with respect thereto. By power rotating the rotor assembly, the operating head is made to scan the inner wall surface of the tank in circular fashion and operate thereon. By vertically adjusting the elevation of the manipulator arm with respect to the rotor assembly during such scanning, the operating head is caused to scan the inner wall surface of the tank either in a spiral manner or in a stepped series of circles. Such scanning may be performed up or down the sidewall to inspect, coat, grind, brush, wipe, spray or jet clean the sidewall or select portion thereof when the tank requires cleaning, inspection or maintenance. In certain instances, the operating head may have one or more grinding, welding, drilling or riveting tools operable under computer control to repair or construct select portions of the cylindrical side and bottom (or top) walls of the tank. Other embodiments of the operating head may be employed to inspect and repair select portions of the tank walls and/or to spray or extrusion coat all or select parts of the inside surfaces of the tank walls with plastic or other lining material. In another embodiment or method, the manipulator may be computer controlled to handle and fasten construction material(s) such as accurately shaped panels, together to automatically construct the same tank it is intended to maintain and clean, without the expenditure of human labor.

The manipulator may be centrally supported or mounted within the tank or reactor and secured therein, or it may be overhead supported above an opening in the tank and operated in a suspended condition. In the former case, the laterally extending manipulator arm or articulated arm assembly is mounted on an axially disposed rotor assembly either anchored centrally to the bottom wall or floor of the tank or reactor or secured to a fitting held in or against the bottom wall. The overhead carriage may travel on a monorail or dual rail conveyor such as a bridge crane which may operate to dispose such manipulator in selected ones of a plurality of tanks under computer control. In both embodiments, the rotor assembly is rotated to thereby cause the operating head of the manipulator to scan close to or contact the cylindrical surface of revolution defining a side wall of the tank.

In an embodiment where the manipulator is suspended overhead, the manipulator comprises a rotor assembly rotatably mounted on an overhead carriage. A vertically extending section of the rotor assembly oriented downward into the tank supports a laterally extending manipulator arm or assembly of articulated arms. The overhead carriage may be supported for two directional movement along an overhead monorail or dual rail system as well as by a bridge crane enabling lateral positioning of the carriage above a selected tank. The manipulator may be automatically operated to perform the described functions with respect to a plurality of storage and processing tanks and/or reactors disposed next to each other in one or more rows. If such tanks are open, the manipulator may be predeterminately aligned above the tank and the extendable section of the rotor assembly lowered therein. The manipulator arm assembly may then be power rotated about the central axis of the tank to cause its operating head to coat, brush, and/or spray or jet clean the cylindrical surface of the side wall of the tank in parallel-circular movements and/or helical scanning movements. For such cleaning, repair, or inspection of the flat bottom wall of the tank, the manipulator arm may also be pivoted with respect to the extendable section. The manipulator arm is then automatically driven to the bottom, and the operating head or heads thereof made to scan a select area or areas of the bottom wall of the tank or to scan and operate on the entire surface thereof in concentric circular or spiral bath scanning under computer control.

Other objects, features, and advantages of the invention will become evident in light of the following detailed description considered in conjunction with the referenced drawings of a preferred exemplary embodiment according to the present invention.

DETAILED DESCRIPTION OF THE INVENTION

Figure 1:
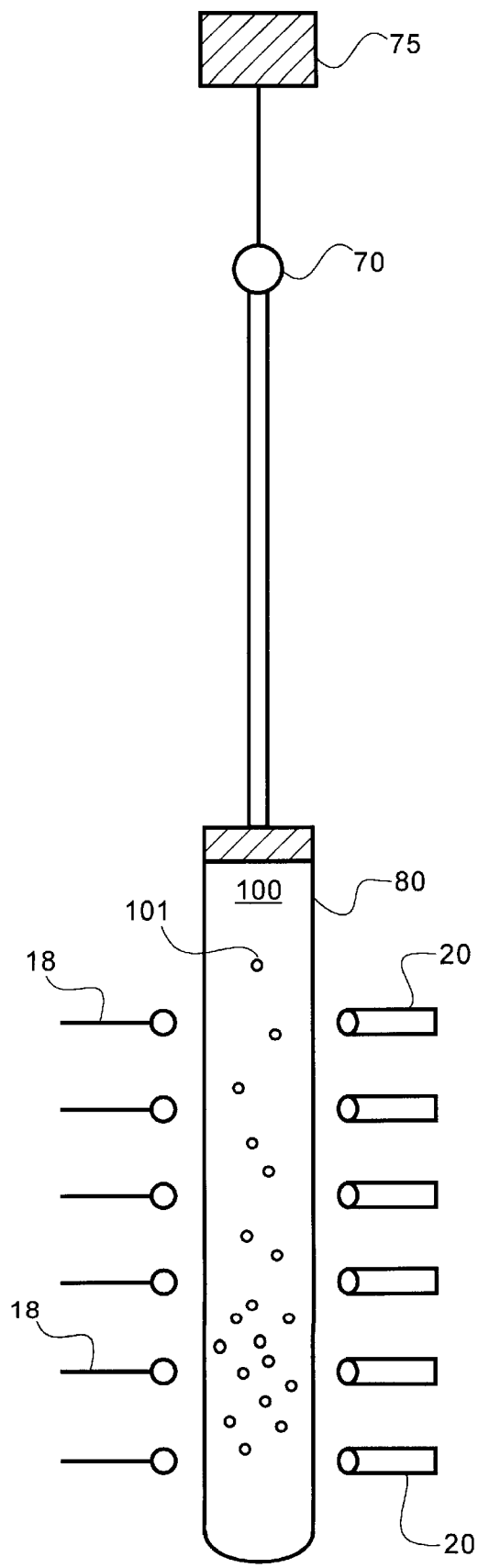
FIG. 1 shows a laboratory type centrifuge for separating components into layers within the centrifuge tube.

FIG. 1 illustrates the present invention as applied to a typical centrifuge for separating biological components, such as cells or organelles, in a heterogeneous mixture. The centrifuge comprises a centrifuge tube 80 which is rotated with a counterweight 5 about an axis defined by a rotor 70 which is driven by conventional mechanical drive means. The mixture 100 is contained in centrifuge tube 80 and may or may not include an additional medium for setting up density gradients within the tube. Mounted in fixed relation to the tube 80 so as to rotate along therewith is an array of lasers 20 and photodetectors 18 for monitoring the presence of test particles 101 within the mixture. Test particles 101 may consist of molecules or particles conjugated to molecules having specific spectral absorption or scattering characteristics so as to give a spectral signature detectable by photodetectors 18. One type of molecule which may be conjugated to the test particle is a fluorescent label such as fluorescein or rhodamine which are commonly used in flow cytometry. The test particles are then detected by means of a laser L for exciting the fluorescent dye molecules and a photodetector P for measuring the light scattered and/or emitted by the fluorescent molecules. The laser is operated in a scanning fashion so that the beam intersects with a large portion of the fluid passing by. The signal produced by the photodetector P varies in accordance with the quantity of test particles present in the mixture and is fed to computer 11.

Figure 3:
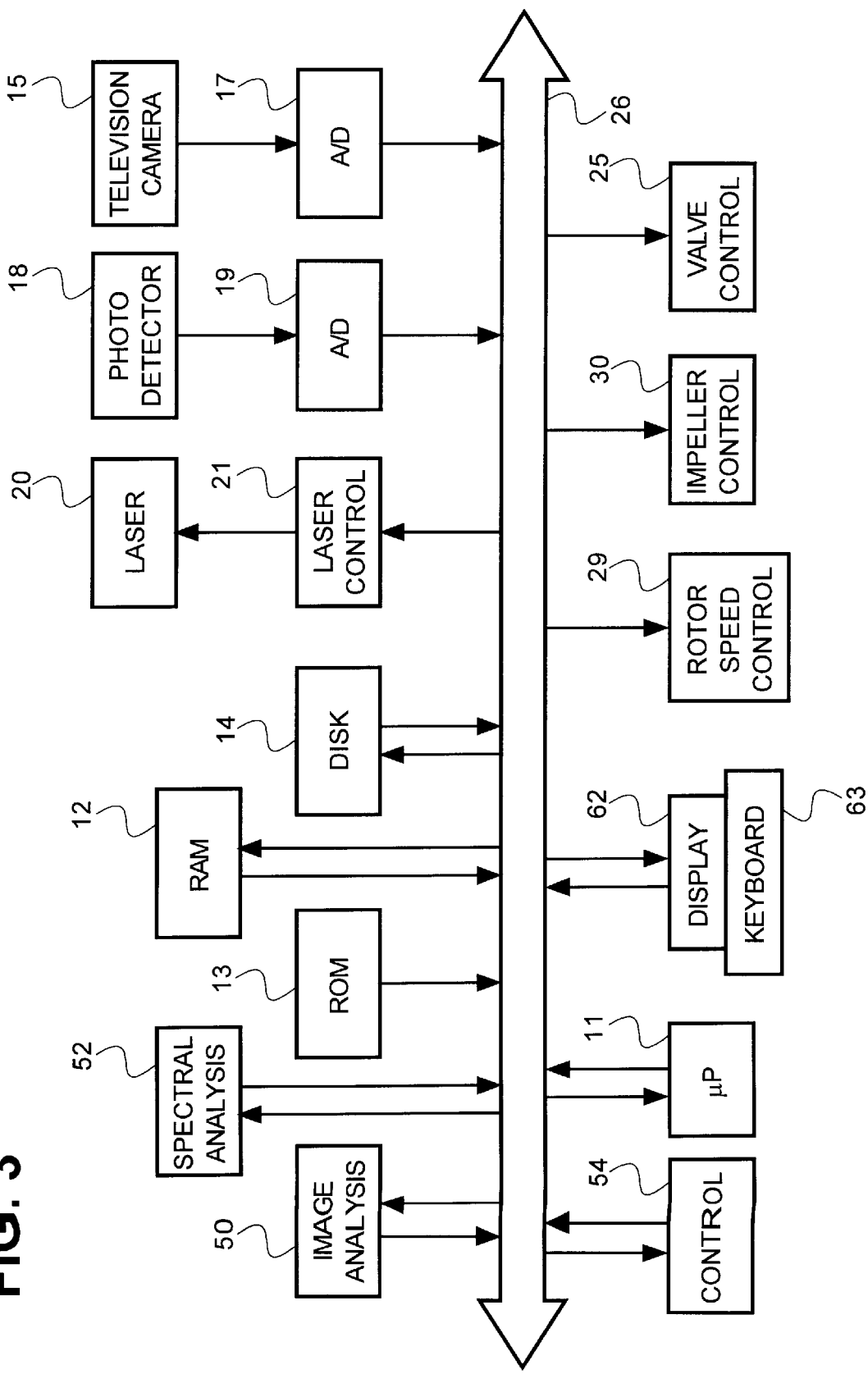
FIG. 3 shows an exemplary computer system for controlling the operation of a centrifugal separator.

The centrifuge in FIG. 1 is controlled in its operation by a computer 11 as shown in FIG. 3 at a speed and for a duration which results in the localization of the test particles 101 in a desired sedimentation layer of tube 80. To accomplish this, the computer is supplied with the data generated by photodetectors 18 which places the location of the test particles 101 in the tube 80. The test particles 101 are chosen so as to have a sedimentation constant approximately equal to the actual mixture component of interest which it is desired to localize at a given layer. The component of interest may consist of large particulate components, such as whole cells, or particular molecules. The location of the test particles thus corresponds to the location of the component of interest. In some applications, the component of interest may consist of detectable particles allowing for direct localization without the need of test particles.

Figure 2:
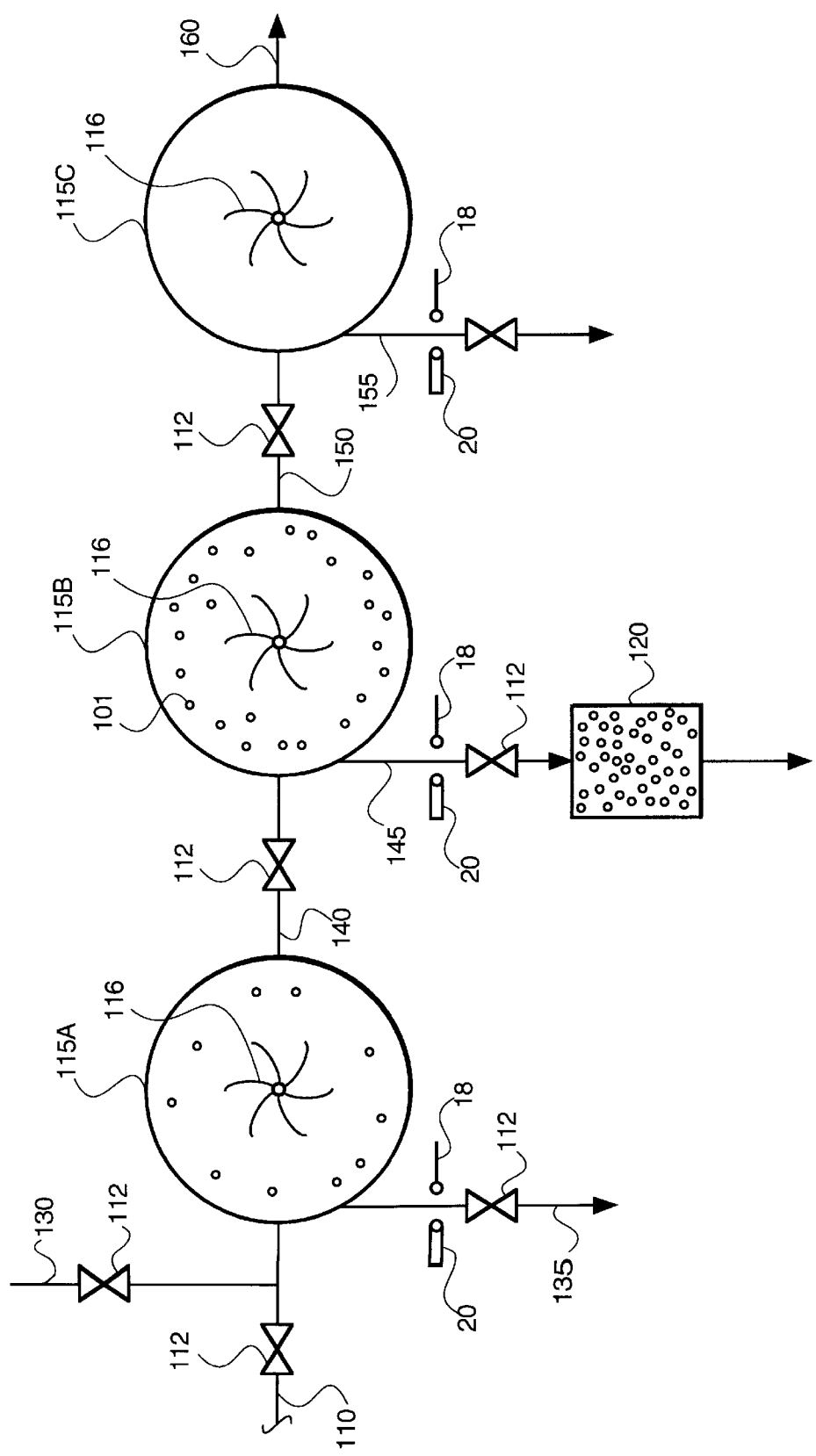
FIG. 2 shows an exemplary multi-stage centrifugal separator for stripping dense components from a feedstock stream.

An exemplary multi-stage centrifugal separator is illustrated schematically in FIG. 2 which includes stages 115A through 115C through which a feedstock fluid flows. The feedstock fluid flows initially as stream 110 into the housing of centrifuge stage 115A where it is made to rotate by impeller 116. The denser components of the feedstock fluid sediment faster than lighter components toward the periphery of the housing and accumulate there. A stripping stream 135 removes these dense components from the feedstock which then flows consecutively to stages 115B and 115C which operate similarly so that components of next higher density are removed by stripping streams 145 and 155, respectively. The feedstock emerging as product in line 160 has thus been progressively stripped of dense and rapidly sedimenting components. The most dense components come off in the first stage, the next densest in the next stage, and so on. The exact density of the fluid in each of the streams 135, 145, and 155 for a given feedstock, however, depends on a number of variables including the speed of the impellers and the rate at which fluid flows between and out of the stages. By controlling these variables in accordance with appropriate feedback signals, the separator may be operated so as to maximize (or minimize) the quantity of fluid components having a particular density in a particular stream. To provide the feedback signals, test particles are injected into the feedstock by stream 130, and their concentrations in streams 135, 145, and 155 are monitored using lasers 20 and photodetectors 18. Test particles may also be used which are detectable by other means such as optical scanning of the fluid to form images and scintillation counting of radiation emitted by radioactively labeled test particles. By whatever means the test particles are detected, the resulting data signals from the test particle sensors are fed to a computer which then adjusts valves 112 controlling the flows in the various streams and the impeller speeds of the stages in a manner so as to result in the desired concentration of test particles in a particular stream. As described above, the test particles are designed to have the same sedimentation constant as the component of interest so that the latter's concentration is necessarily also controlled. A plurality of different types of test particles may also be employed to control the concentrations of a plurality of components.

In certain applications of the invention, the component of interest may itself be detectable so as to obviate the need for test particles. For example, if centrifugal separation is used to remove radioactive particles from water, the concentration of radioactive particles in a particular stream may be directly monitored with a scintillation counter. Other components of interest may be directly detectable by other means.

If the separator is operated so that a particular component of interest is maximized in a product, the product necessarily contains a high concentration of test particles. It may be desireable to remove these test particles from the product. Such removal of the test particles cannot by accomplished by differential sedimentation or filtering without also removing the component of interest, however, due to their deliberately similar size and density. The test particles may therefore also include a ligand having a binding affinity for a specific molecules immobilized in a reaction column. Such a reaction column 120 is shown in FIG. 2 as removing the test particles from stream 145. Examples of molecular binding pairs which may be employed include complementary nucleic acid sequences, avidin/biotin, and lectins/carbohydrates, with one member of the pair being immobilized within the reaction column and the other conjugated to the test particle.

FIG. 3 shows an exemplary system for controlling the operation of a centrifugal separator such as illustrated in FIG. 2 in accordance with the present invention. A microprocessor or computer 11 controls the test particle detection and control actions by receiving and gating digital detection and control signals to and from various electrically operated devices and subsystems. The microprocessor 11 is shown as connected via bidirectional data bus 26 to various peripheral components including RAM 12, ROM 13, disk storage device 14, keyboard 63, display 62, as well as other components as described below. Scanning a fluid to detect test particles is effected by one or more imaging devices and/or spectral radiation detection devices such as photoelectric detector 18 which may be used alone or with a plurality thereof and one or more attendant lasers 20 to scan across a duct such as a pipe through which a mixture whose components are to be separated is flowing. The output of detector 18 is a variable electrical signal which is digitized by an analog-to-digital converter 19 and passed to data bus 26 for analysis by a spectral radiation analysis module 52. Similarly, the output of a television camera 15 is passed via analog-to-digital converter 17 to the system for analysis by image analysis module 50. In a preferred embodiment, the computed digital code signals output by either or both the image analyzing and spectral radiation signal analyzing modules 50 and 52 are applied by microprocessor 11 to a control module 54 for analysis using expert systems, fuzzy logic and/or neural network techniques, where the aforementioned modules may be either dedicated hardware components or software programs. The output of the control module 54 is then used to optimize the operation the centrifugal separator by controlling the operation of various fluid flow control valves through a valve control 25, controlling the adjustment of the impellers for each centrifuge stage through impeller angle control 30, and the speed of each centrifuge stage through impeller speed control 29.

A mixing apparatus in accordance with the present invention includes an array of sensors for monitoring the flow of material within the mixing vessel. By whatever means the flow patterns are detected, the resulting data signals from the flow sensors are fed to a computer which then adjusts valves controlling the flows in the various streams, baffles in the mixing vessel, and the speed and angle of a mixing impeller in a manner so as to enhance the mixing process.

Scanning a fluid to detect flows is effected by one or more imaging devices and/or spectral radiation detection devices such as photoelectric detector which may be used alone or with a plurality thereof and one or more attendant lasers to scan across the mixing vessel or a duct such as a pipe through which materials to be mixed are flowing. The output of the detector is a variable electrical signal which is digitized by an analog-to-digital converter and passed to data bus for analysis by a spectral radiation analysis module or computer. Similarly, the output of a television camera is passed via analog-to-digital converter to the system for analysis by an image analysis module. In a preferred embodiment, the computed digital code signals output by either or both the image analyzing and spectral radiation signal analyzing modules are applied by a microprocessor to a control module for analysis using expert systems, fuzzy logic and/or neural network techniques, where the aforementioned modules may be either dedicated hardware components or software programs. The output of the control module is then used to optimize the operation of the mixer by controlling the operation of various fluid flow control valves, controlling the adjustment of baffles, controlling the adjustment of impellers, and controlling the speed of the impeller.

Another embodiment uses a television camera for imaging the individual components of the material within mixing vessel in those applications wherein particulate matter is to be mixed with another material which permits light to be transmitted therethrough. The particulate matter within the material can then be imaged to ascertain the status of the mixing process. The camera is directed at the surface of the material within the vessel, and the distribution of particulate matter within the rest of the material is obtained by varying the depth of focus of the camera. In other embodiments, a surface image alone may suffice. The image data produced by the camera is then fed to the computer which effects control of mixing process variables as described above in order to enhance the mixing process.

The distribution of the material components being mixed within the mixing vessel may also be ascertained via tomography. An array of tomographic transmitter/detector pairs are arranged around the periphery of the vessel. The transmitter portion of each transmitter/detector pair transmits radiation through the material within the vessel, and the radiation attenuated by its passage through the material is then detected by the corresponding detector portion of the pair on the opposite side of the vessel. The type of radiation employed varies with the nature of the material but needs to be radiation which is differentially absorbed by the different components of the material being mixed. Examples of radiation exhibiting such differential absorption for many materials would include electromagnetic radiation (eg., X-ray, gamma, ultraviolet), particle radiation (eg., neutron, beta), and ultrasonic radiation. Like medical X-ray computerized axial tomography (CAT), tomography in this application is based on measurements of the attenuation of photon beams (where electromagnetic radiation is employed) in several directions as they pass through the medium being imaged. On the basis of each measurement, the integral of the medium's density function is determined along a line between the radiation source and its corresponding detector. These measurements form the basis for the mathematical reconstruction of the cross-sectional density of the medium. Medical CAT scanners utilize a rotating X-ray source and a circle of detectors. In the present application, however, a system involving a rotating radiation source cannot be used, because the flow patterns occurring within the mixing vessel change much too rapidly. All measurements must therefore be carried out simultaneously by a set of fixed transmitter/detector pairs.

The flow patterns within the mixing vessel, rather than the distribution of components themselves, may also be used to monitor the adequacy of the mixing process. As described above, there exists for any particular mixing application a flow pattern or patterns involving both bulk fluid and turbulent flow which serves to enhance the mixing of components. In order to determine what kind of flow pattern exists at any given time within the mixing vessel, the velocity components of a plurality of volume elements within the vessel must be ascertained. One way to do this is by laser scanning. In a particular embodiment, probes are positioned at points around the periphery of the vessel so as to direct laser radiation beams into the material within. Each such probe comprises transmitting and receiving optics within the probe for transmitting laser radiation received from a laser into the vessel and receiving radiation backscattered by particles therewithin. The technique used in this embodiment is to illuminate the particulate matter flowing within the vessel with laser light and then collect and process the light scattered thereby. Owing to the Doppler effect, moving particles will affect the frequency of the scattered light in accordance with the magnitude and direction of the particle's velocity.

Each probe splits the laser radiation received from the laser into two beams of equal intensity which are focused at a common point in the material flowing within the vessel. An interference pattern is formed at the point where the beams intersect which defines the measurement volume. Particles moving through the measurement volume scatter light of varying intensity, some of which is collected by the probe (in the form of beams along the same path as the beams) and passed to a photodetector. The resulting frequency of the photodetector output is directly indicative of the magnitude and direction of the particle's velocity. It should be appreciated that the velocity component measured at the intersection of the two beams is perpendicular to the axis of the probe (ie., the common axis of the beams) and perpendicular to the plane of the beams. In order to measure three velocity components corresponding to three orthogonal axes, three probes may be used to transmit and receive laser light of different frequencies generated by lasers. Optical filters within each probe serve to eliminate all radiation except for a range of frequencies centered about the frequency of the light generated by the probe's corresponding laser. In order to scan the entire volume of the vessel, each probe contains a movable mirror or prism for varying the direction of the transmitted and collected beams as well as a movable lens for varying the focal point of the beams in accordance with control signals received from a computer. Such movable mirrors and lenses are powered by electromagnetic devices commonly used in the laser scanning art. The computer controls the operation of the probes so as to scan the entire volume of the vessel and thereby ascertain the flow pattern occurring at any given point in time. In accordance with the optimum flow characteristics for mixing the particular components within the vessel (which flow pattern can be determined by conventional analysis well-known to those of skill in the art), the computer adjusts the process variables to enhance the mixing process in the manner described earlier.

Other embodiments of the invention may employ laser scanning to irradiate matter within the mixing vessel and thereby generate fluorescent radiation depending upon the nature of the matter being irradiated. In this manner, similar to the imaging techniques discussed above, the distribution of the components being mixed may be components components fluoresce at different frequencies) by spectral analysis and the mixing process controlled in accordance therewith.

Another aspect of the invention relates to a system and method for automatically performing or conducting experiments or analyses, such as experiments associated with research and development. In particular, the invention is directed to a system and method for conducting a variety of experiments such as chemical, medical or biological, metallurgical, physical, electrical, or other types of experiments whereby the results thereof are detectable by one or more means such as electronic or bio-electric sensors, vision systems employing television camera scanning and analysis, magnetic field or spin resonance detectors, radiation detectors, laser spectroscopic scanning, X-ray detectors or any suitable form of detector or scanner which will detect variations in one or more variables such as chemical composition, physical structure or color, biological composition or shape or any other variable which during an experiment or test may be detected in a manner to generate electrical signals either in digital form or in analog form capable of being digitized or otherwise converted to a form which may be automatically analyzed by a computer. The apparatus and method defined herein may also be employed to automatically determine, by means of scanning or sensing and computer analysis, the results of varying test variables on materials or articles of manufacture, as such variations occur, for performing a variety of non-destructive tests thereon wherein such results, generated in the form of electrical signals, may be processed and utilized for predicting ultimate test results or further variations in the biological or chemical structure of matter without the necessity of carrying the tests further or to a point whereby the material, matter, or article is destroyed or adversely affected.

In one form of the instant invention, an article, inanimate material, biological cell or specimen, living organism or plant life is subjected to one or more variations in environment for an extended period of time. For example, the specimen may be subjected to one or more chemical and/or biological agents by disposing it in a container of such chemical or biological agents, flowing or flooding the agents on or into the specimen, injecting the agents therein or otherwise applying a controlled amount or amounts of a chemical or chemicals thereto. The specimen may also be subjected to one or more forms of radiation of constant, intermittent or variable intensity and/or frequency, such as X-radiation, gamma radiation, laser or other form of light radiation, electromagnetic field radiation, electrical energy or other form of radiation. The specimen may also be subjected to mechanical force such as pressure or force applied to its surface to compress, bend shock or otherwise affect same. The specimen, material or article may also be subjected to heat or cryogenic temperatures, to vibrations such as ultrasonic vibrations, to changes in atmosphere or to the effects of certain living organisms such as select cells, viruses, or viral and/or delta particles.

Both the subjection of the specimen or material to such changes in environment and the detection or sensing of the effects of such changes in environment are controlled by a master controller such as a digital computer which also serves to receive the signals indicative of such changes, process such signals, track or determine variations which occur with time in the chemical or physical structure of the specimen or its affect on the sensor or sensing system employed wherein such results may be utilized to control the carrying out of further testing and, in certain instances, vary the experiment or tests so as to optimize or otherwise affect the experiment and the results obtained therefrom. Fuzzy logic and neural network computing circuits may also be employed to optimize and complete the test or experiment.

In a preferred form of the instant invention, a specimen of material which may comprise a chemical, a group of chemicals, living or dead biological specimens such as one or more living cells, section of tissue, experimental animals, plant life or other form of biological material, is subjected to a variation or variations in its environment wherein such variation or variations may comprise subjecting the specimen to one or more chemicals in solid, liquid and/or gaseous form, one or more biological specimens or biological elements such as proteins or enzymes, or one or more variations in radiation or radiation field, which variations may cause variations in the chemical, physical or biological nature of the specimen. The specimen is scanned, either continuously and/or intermittently, by an electronic scanning device such as the read beam of a television camera or flying spot scanner raster or otherwise scanning all or part of the specimen. Or an image of the specimen generated, for example, by a scanning electron microscope, may be so scanned to generate output signals which vary in accordance with variations in the image of the specimen such as variations in its shape, size, surface structure, color, transparency, arrangement and shape of components thereof, etc. Such variations result in variations in the amplitude and/or frequency of the video signal generated by the television camera or scanner which signal or signals are electronically processed, such as by digitizing, and the results thereof compared with signals recorded in a master memory so as to indicate, by generating other signals, the degree or type of variations occurring in the specimen during the experiment. Such television camera scanning may be supplemented or replaced by deflection controlled laser beam scanning wherein reflection and/or fluorescence radiation may be photoelectrically detected to generate image and/or spectral scanning signals which are computer processed and analyzed to attain the results described herein.

The results so obtained, which are in the form of coded electrical signals, may be applied to perform such functions as controlling the driving of a display or displays for indicating such results, controlling the operation of a hard copy printer for printing such results, selectively activating a speech synthesizing circuit or circuits to generate synthetic speech indicative of the results, or control one or more devices such as motors or solenoids, switches or other devices for controlling the experiment thereafter. The results may also be employed to control medical devices or machinery or to apply remedial means for correcting or changing a condition or developing condition in a machine, biological specimen or living being.

In another form of the invention, a plurality of sensors are disposed with respect to a specimen under test and are operable to collectively sense the shape of the specimen and generate a plurality of electrical signals which are indicative of the shape of the specimen. Such signals are electronically processed to generate code signals indicative of the specimen shape at any particular time for use in computer analyzing the effects of variations in environment on the specimen. Similarly, a plurality of the same or different sensors may be employed to sense variations in electrical resistivity indicating, for example, variations in composition or dimension of a specimen, such as strain resulting, for example, from variably loading the specimen with force or forces applied thereto. The electrical signal outputs of the sensors are electronically processed, such as by digitizing, and operations or calculations are performed with respect thereto for providing a computer with such information wherein the computer controls the operation of one or more devices which vary the parameters of the test or experiment in a predetermined manner to optimize or determine the final results thereof.

A television camera may be utilized to scan the any selected portion of a specimen depending on the focusing of the lens of the camera. Camera 16 may also be utilized in conjunction with a sample analysis system to scan microscopic images of samples. The video signal output of the camera is passed to an analog-to-digital converter which digitizes the signal and generates digital codes representative of pixel color and brightness information, which codes are conducted to a computer for recording in its archival memory together with signals identifying the specimen received from memory and time and date indicating codes received from a digital time signal generator. As a result, the coded or digital image signals may be later automatically compared with similarly recorded image signals derived from scanning similar portions of the patient during prior times, as retrieved from archival memory. The results of such analysis may be entered in the data memory while images derived from such television scanning may be instantly viewed by reproducing same from an erasable memory adapted to receive the output of the analog-to-digital converter, such as a RAM or shift register, the output of which is connected to a digital-to-analog converter. Data generated, including the results of tests, status of tests, or experiments or any other data which is necessary or of assistance to a programmer or operator of the system, may also be displayed on a monitor.

In another embodiment, a thermographic camera or thermography scanner which is provides on its output analog signals representative of image information defining the distribution of body heat generated by a human being, which information may be recorded in analog form or digitized and recorded in an archival memory or compared with previously generated thermographic information recorded in such memory. The results of such comparison and analysis of the output of the thermographic scanner may be passed to a data memory while the images of either or both present and past thermographic scans of the human body or select portions thereof may be presented on the display screen of the monitor. Similarly, digital data representative of images derived from a CAT scanner may also be recorded in the archival memory 28, selectively reproduced therefrom and presented to scan memory 41 or compared with signals generated in effecting past CAT scans in an analysis operation which is controlled by a computer. The results of such analysis may also be stored in a data memory and/or displayed as a CAT scan image on a monitor.

The system may also provide for the sensing of environmental parameters the quantitative value of which may be recorded and used in analysis and diagnosis. A forced air blower may be provided to cause a constant flow of air from the outside of the housing containing the specimen to be passed over a humidity sensor, such as a and a temperature sensor, such as a thermistor, both of which are contained within an air duct. The sensors generate signals which are indicative of the respective environmental parameters sensed, which signals are converted to digital codes by respective analog-to-digital converters and passed therefrom to a computer for inclusion in the automatic analysis and recording operation controlled by the microprocessor. Air pressure may also be sensed by an air pressure sensor which produces output analog signals which are converted to digital codes by an analog-to-digital converter and transmitted to the computer for recording under its control as well as automatic analysis.

Specimen temperature may be sensed by a temperature sensor, such as a thermistor, which provides signals representative of such temperature, which signals are converted to digital codes by an analog-to-digital convertor and are conducted therefrom to the computer which controls the analysis and recording of such signals. In the case where the specimen is a human subject, blood pressure may be sensed by one or more sensors which provide output signals indicative of systolic and diastolic blood pressure which signals are converted to digital codes by an analog-to-digital convertor and passed to the computer for automatic processing and analysis. The computer also generates on-off drive signals for controlling the operation of a motor driving an air pump. Such pump delivers air pressure to the air pressure cuff of a blood pressure measuring device through a flexible hose and inflates such cuff to effect such blood pressure measuring operation. Tonometric blood pressure measuring means may also be employed. The system may also include a body fluid analyzing system and a histological analyzing system, both of which are interactive with the computer and provide digital information on their respective analyses, which information may be compared, further analyzed or recorded for future display and analysis.

The system may also be operable in a manner to display or print data relating to additional test procedures and/or patient information required, which will be dependent upon the results obtained during a testing cycle. The system may also contain adaptive electronics operable to alter its mode of operation in order to obtain a proper diagnosis. The operation of the system may then be controlled or affected by programming of the microprocessor and computer in a manner to effect functions defining or resulting from the employment of artificial intelligence techniques such as are described below.

The artificial intelligence control of functions of the present invention will be described with respect to an exemplary system embodiment which may comprise any of various medical imaging apparatus and chemical analyzing equipment for providing the raw data inputs to the rest of the system. The control subsystems to be described are information processors which may consist either of dedicated hardware modules, separate program modules running on a single computer, or any combination thereof. Data is input to the system from a data input device which represents any type of imaging or sensing device which produces information regarding physical phenomena in a form suitable for inputting to a computer. Thus the input device represents not only the imaging or sensing device itself but also any associated signal processing devices such as a digital-to-analog converter.

In the case of image-type input data, images of either a tissue sample or a selected anatomical region of the patient's body are first converted to digitized form suitable for computerized analysis. Depending upon the particular type of imaging modality employed, the digitizing step may be performed by the imaging apparatus itself. In computerized axial tomography (CAT), positron emission tomography (PET), and magnetic resonance imaging (MRI) scanners, for example, digitization is inherent in the image generation process. Other types of imaging devices such as, for example, television cameras, B-mode ultrasonic scanners, scanning electron microscopes, or thermography scanners, may produce pixel intensity values in analog form which need to be digitized before further processing. In any case, each image input to the system consists of an array of digital pixel intensity values which, when converted to analog gray scale values, may be used to drive a CRT and thus provide a visual display of the image.

The digitized image is then input to a feature extractor which converts the image data into useful measurements. (As explained below, the feature extractor operates similarly on non-image input data.) In order to extract such features, the image data is first subjected to a segmentation process which groups the pixels of the image into distinct entities representing separate organs, parts of organs, tumors, or other anatomical structures. Such segmentation may be accomplished by methods well-known to those of skill in the computer vision art such as: (1) edge-based approaches where intensity discontinuities are detected, and the pixels are then clustered into regions bounded by the detected edges, (2) textural segmentation approaches where the image is partitioned into non-overlapping regions based on textural homogeneity of groups of pixels which may involve, for example, either region growing by sequentially adding similar pixels to a local starting point, or region splitting where the entire image is sequentially divided into smaller regions on the basis of pixel intensity dissimilarity, or (3) matching approaches utilizing a standard image of the same anatomical region where the organs and anatomical structures of the standard image are used as templates for matching with analogous structures in the input image. A feature extractor in accordance with the present invention may make use of any or all of those methods as well as other pattern recognition methods such as neural networks. The feature extractor may also provide for user assisted segmentation where the image is displayed to an operator who then defines the relevant anatomical structures by means of, for example, a cursor or light pen in response to prompts from the system.

After the segmentation process, the feature extractor then processes the image data into information which is useable by the system in performing clinical diagnosis or other types of reasoning. Such information will typically include the size and shape of the segmented regions as well as the spatial distribution of a pattern of intensities over a particular region (ie., its texture).

As aforesaid, the system may also include non-imaging diagnostic testing modalites such as blood pressure and heart rate monitoring, temperature monitoring, electrocardiogram (EKG) monitoring, and equipment for automatically performing a sequence of laboratory tests upon samples of tissue, blood, urine, other bodily fluid, or any other type of substance which can be tested and/or analyzed so as to generate a quantitative measurement. In such a system, the results of each test performed are output in the form of an electrical signal which is digitized and input to a feature extractor 102 similar to that described above with respect to image processing. A feature extractor for non-image data is usually quite simpler than for image data since, in many cases, the amplitude of the signal (ie., the laboratory value, such as hematocrit, blood gas measurement, serum glucose, antibody titers, etc.) is all that is of interest. Complicated input signals, on the other hand, such as an EKG waveform, require extraction of features in a manner similar to that described for image data.

The resulting extracted features from the input data (hereinafter referred to as a feature vector) are next input into a data interpreter which evaluates the significance of the features in relation to a specific knowledge domain such as clinical medicine. In a preferred embodiment, the data interpreter is a rule-based artificial intelligence program of a type sometimes referred to as a production system or an expert system. The data interpreter would then comprise 1) a knowledge database consisting of a set of rules or productions which allow the production of new information on the basis of currently known facts, 2) a fact database containing facts which include image and non-image feature vectors, and 3) a control program, such as an inference engine, for determining the applicability of the rules in the context of the current database, the selection of appropriate rules, and operating on the fact database by means of the selected rules.

In accordance with the present invention, the fact database comprises feature vectors generated from image and non-image input data as well as other relevant parameters manually input into the system which are determined by other means such as, in the case of a medical data interpreter, physical examination or from a patient's medical history. In a particular embodiment, the fact database may also contain comparison codes which are generated by a comparison module which represent differences between a presently input feature vector and various stored feature vectors. Such stored feature vectors may, for example, be those extracted from a previous sensing cycle or image field scan of the same anatomical region of the same patient in which case the comparison code may represent a change in the patient's condition as reflected by detectable changes between present and past image phenomena. Comparison codes may also be used to represent the difference between the patient's scanned image and a standard or normal image of the same anatomical region. Similarly, for non-image feature vectors, difference or comparison codes may be generated by comparing the resultant value of the test with standard norms and/or codes defining results of past tests on the same patient.

The knowledge database contains the logic used by the system in evaluating the clinical significance of the feature vector. Each rule of the knowledge database is typically in the form of an implication or IF-THEN statement. Each such rule thus has a premise and a conclusion where the premise may consist of any number of clauses representing factual statements or conclusions which are combined disjunctively or conjunctively. When the premise is satisfied, the rule is "fired," and the rule's conclusion is taken by the system to be true. That conclusion may then be used by the system in activating other rules and so on. The rules thus represent the relationships between clinical parameters, such as image features and laboratory test results, and clinical conclusions based on current medical knowledge. The ultimate clinical conclusions contained in the rules are typically explicit statements reflecting an assessment of the patient's condition and/or recommendations for treatment. Such statements may include, for example, diagnoses such as: "the size of the tumor has increased," "the abscess has disappeared," "hypoglycemia is present," or "lung consolidation indicates pneumonia." Using what is referred to as forward-chaining, database facts, and/or conclusions from applicable rules are linked to the premises of other rules until one or more ultimate clinical conclusions are reached. In the event that no such ultimate conclusion can be verified, the system outputs the premises needed for such a conclusion in the form of a recommendation for further tests or data.

The system may also perform backward-chaining of rules in order to test hypotheses about the patient's condition. In backward-chaining, conclusions are linked to premises containing factual statements, the latter being compared with the fact database. The chaining process is continued until premises are identified which, according to the fact database, establish the conclusion as true. If a premise is identified which, if true, would establish the conclusion, but there is currently no such information in the fact database about that premise, the system asks the user for the needed information in the form of a recommendation for further testing. The hypotheses to be tested may be generated automatically by the system as the product of rules or may be inputted manually by a system user.

Figure 4:
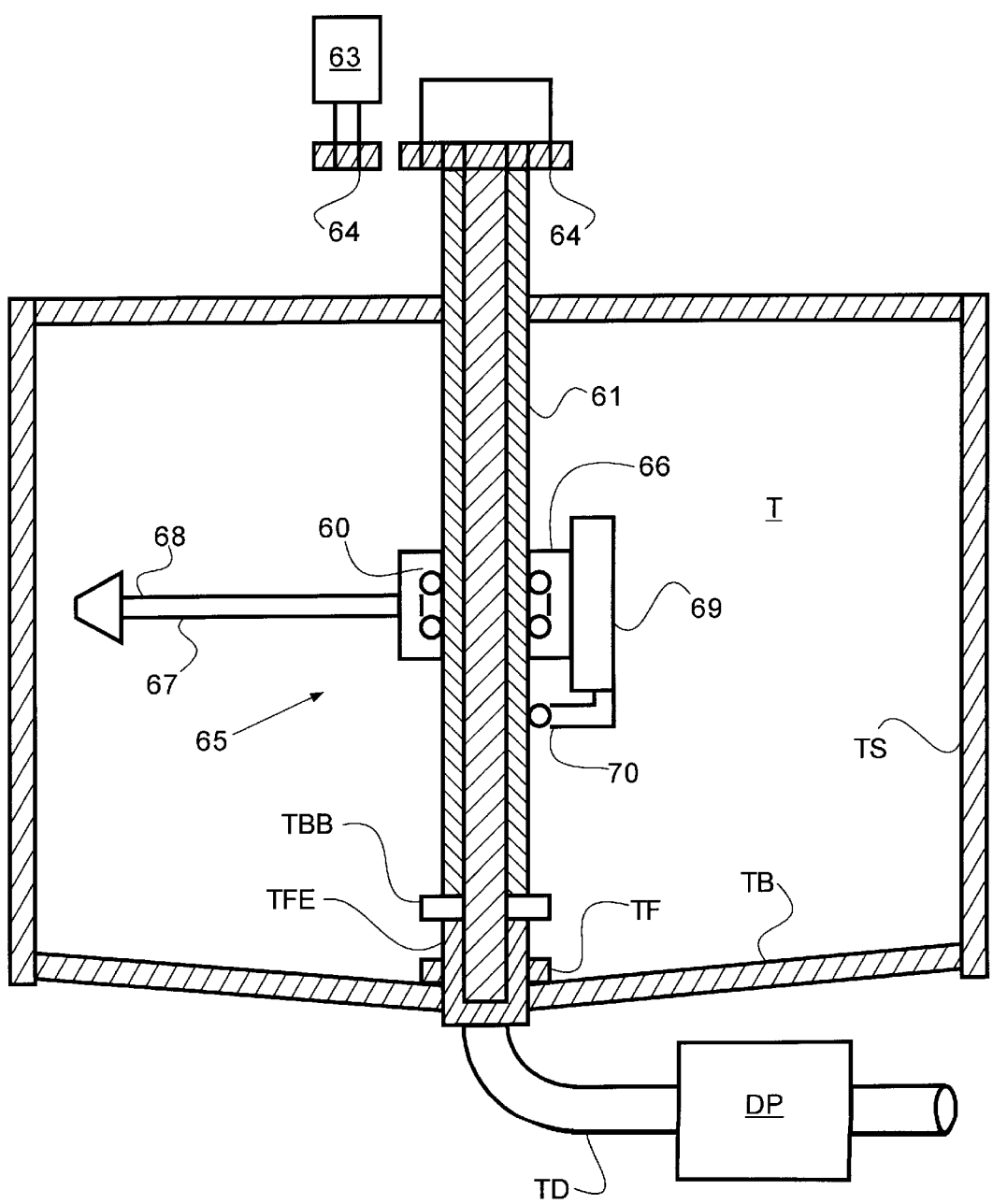
FIG. 4 is a cross-sectional view of a storage tank having a manipulator apparatus in accordance with the invention mounted therein.

Another aspect of computer operated material processing involves the maintenance of vessels such as storage tanks. An embodiment of a computer operated tank cleaning apparatus is illustrated in FIG. 4 where a manipulator apparatus is mounted within a tank T. Tank T is made of plastic, metal or ceramic material, or combinations thereof, defining a cylindrical side wall TS and a centrally sloped bottom wall TB for drainage of liquid from the tank through a drainage fitting TF. Drainage fitting TF is connected to a draining duct TD which is connected to a solenoid valve or drainage pump DP which may be used to recirculate and/or remove the tank liquid on demand as controlled by computer. Fitting TF may have a suitable filter and passageway therethrough for removing and filtering tank liquid.

The manipulator apparatus includes a rigid vertical tubular rotor assembly 61 which is rotatably supported at its lower end by a roller bearing TBB mounted to an upward extension TFE of fitting TF which centers rotor assembly 61 with its longitudinal axis the central axis of the tank. Fixedly mounted at the top of the tank T (by a means not shown) is a manipulator rotation motor 63 whose output shaft is coupled to rotor assembly 61 which is coupled by gears 64 to rotatably drive the tube 61 and a manipulator arm assembly 65 supported thereby about the longitudinal axis of the tank T.

Manipulator arm assembly 65 includes a base 66 in the form of a collar supporting a laterally extending arm 67 having an operating head 68 at its end. The arm 67 contains electrical wires and/or fluid conduits extending therealong for electrically or fluidically power operating one or more devices, as described, in or defining the operating head. A second gear motor 69 has a circular gear 70 on its output shaft, the teeth of which gear engage in a gear toothed track (not shown) formed in or secured to and extending along the length of rotor assembly 61 to drive the arm assembly 65 longitudinally up and down the rotor assembly 61 along a linear ball race 60 to vertically position the operating head 68 within the tank T while it is rotated or held stationary.

Figure 5:
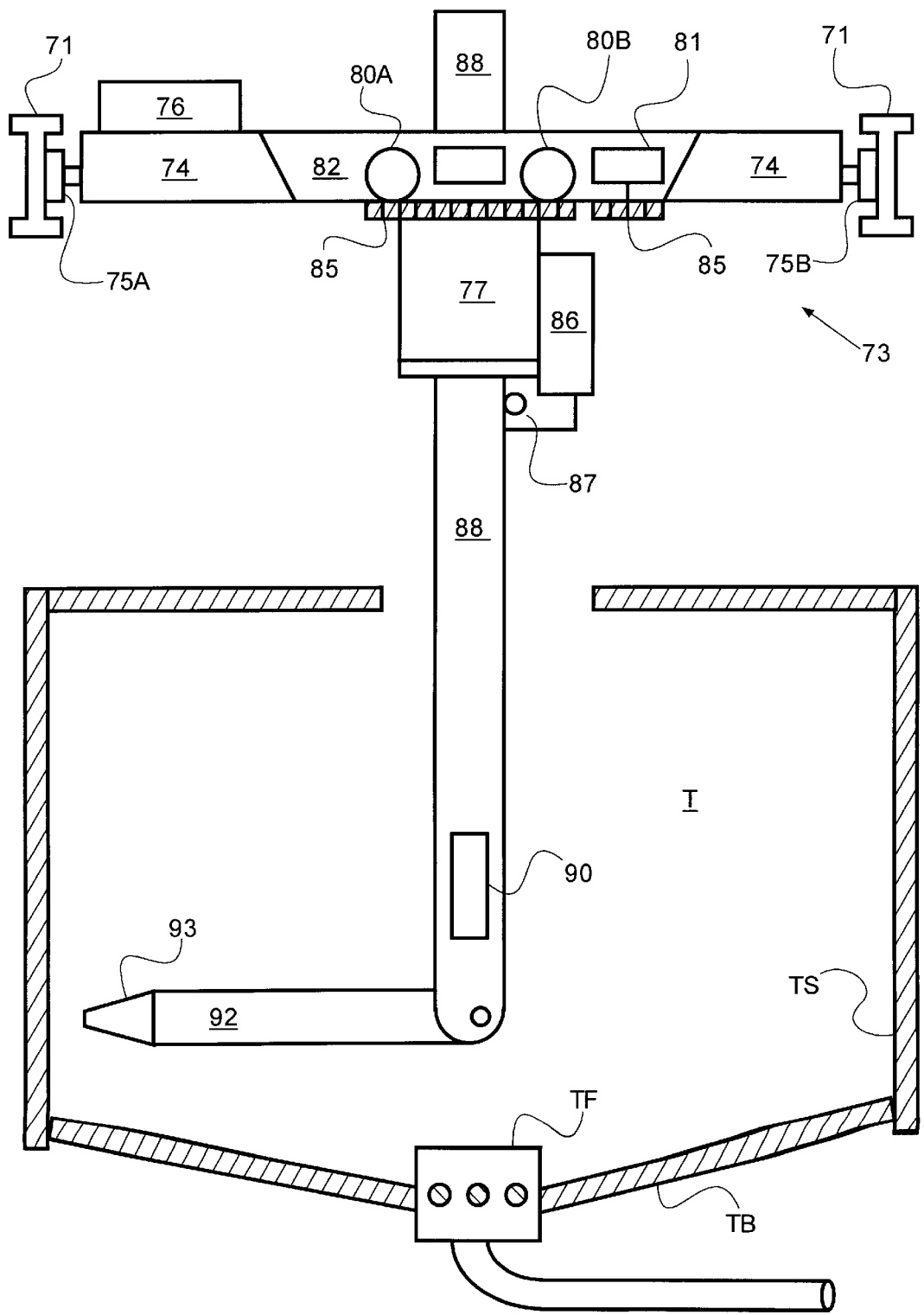
FIG. 5 is a cross-sectional view of a storage tank having a manipulator apparatus in accordance with the invention mounted on an overhead rail system and extending into the interior of the tank.

In FIG. 5 is shown a second electromechanical manipulator apparatus supported by an overhead rail conveyor system which is operated to service a plurality of tanks, one of which tanks TA is shown with a vertical rotor assembly 77 of the manipulator centrally disposed therein and operable to scan, clean, inspect, assemble or otherwise operate on the wall of the tank. The manipulator apparatus includes parallel overhead supported dual rail tracks 71 and 72 along which a bridge crane assembly 73 is adapted to travel preferably under control of a manipulator supervisory computer 50 which employs feedback signals generated by rotary limit switches or other sensors sensing drive motor rotations to predeterminately move and locate the manipulator arm and its assemblies. Wheels 75a and 75b rotatably supported on the lateral bridge 74 of the bridge crane are driven by a gear motor 76 supported by the bridge beam to predeterminately locate the bridge crane assembly with its manipulator rotor assembly 77 centered above the tank TA. A wheeled carriage 82 supports the manipulator rotor assembly 77 subtending therefrom and is driven back and forth along the track defined by the I-beam bridge 74 by a second reversible gear motor 79 supported by the carriage and geared to one or more of the carriage wheels 80A–80B. A third reversible gear motor 81 secured to carriage 82 has its output shaft coupled to rotor assembly 77 through gears 85. Rotor assembly 77 extends vertically down therefrom and is rotatably supported under carriage 82. Movable up and down within rotor assembly 77 and rotated therewith is a splined shaft or tube 88 which is axially driven by a third gear motor 86 secured to the outer wall of rotor assembly 77. A gear 87 on the shaft of motor 86 engages teeth (not shown) formed in the outer surface of shaft 88 to effect such longitudinal driving movement. A rotary joint assembly 91 at the end of shaft 88 supports a manipulator arm 92 which is power rotated about such joint by a fourth reversible gear motor 90 secured to shaft 88. An operating head 93 as described is secured to the end of arm 92 and is positionable thereby next to the cylindrical wall TAW of the tank TA.

Figure 6:
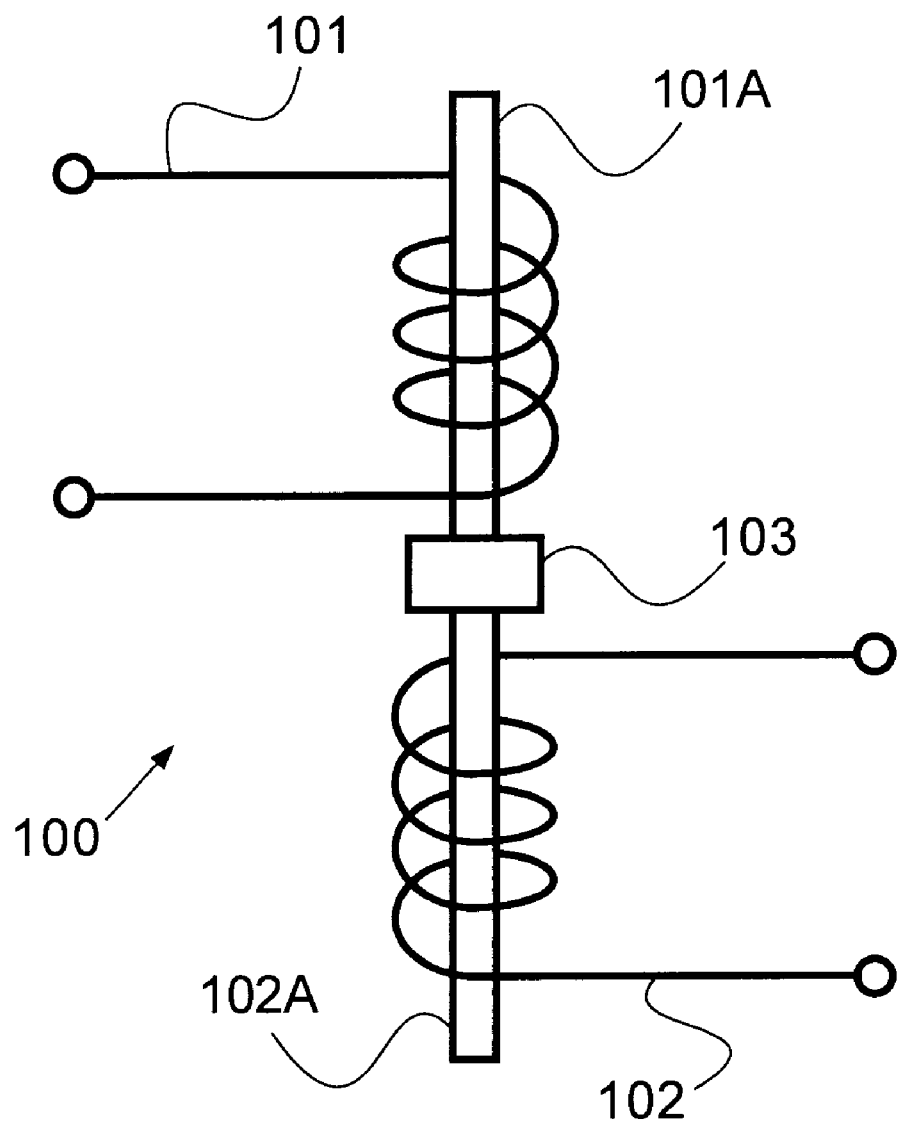
FIG. 6 is a schematic of a means for transmitting AC power from and external source to the rotating rotor assembly of the manipulator apparatus.

In the embodiments described above, electrical power for operating the manipulator arm and the operating head either must be derived from a battery located within the rotor assembly or transmitted to the rotor assembly from an external power source via a rotatable coupling. FIG. 6 shows such a rotatable power coupling 100 in which power is transmitted from a primary transformer winding 101 connected to an AC external power source to a secondary winding mounted on the rotor assembly via rotatably coupled core portions 101a and 102a around which the windings are wound. Core portions 101a and 102a are coupled together through a bearing assembly 103 which enables the core portions to rotate with respect to one another while still maintaining a low reluctance pathway for magnetic flux from the primary winding 101 to flow to the secondary winding 102 and induce an electrical voltage therein. Power is thus supplied to the rotating rotor assembly and the components mounted thereto, including the manipulator arm and operating head, from an external source.

Figure 7:
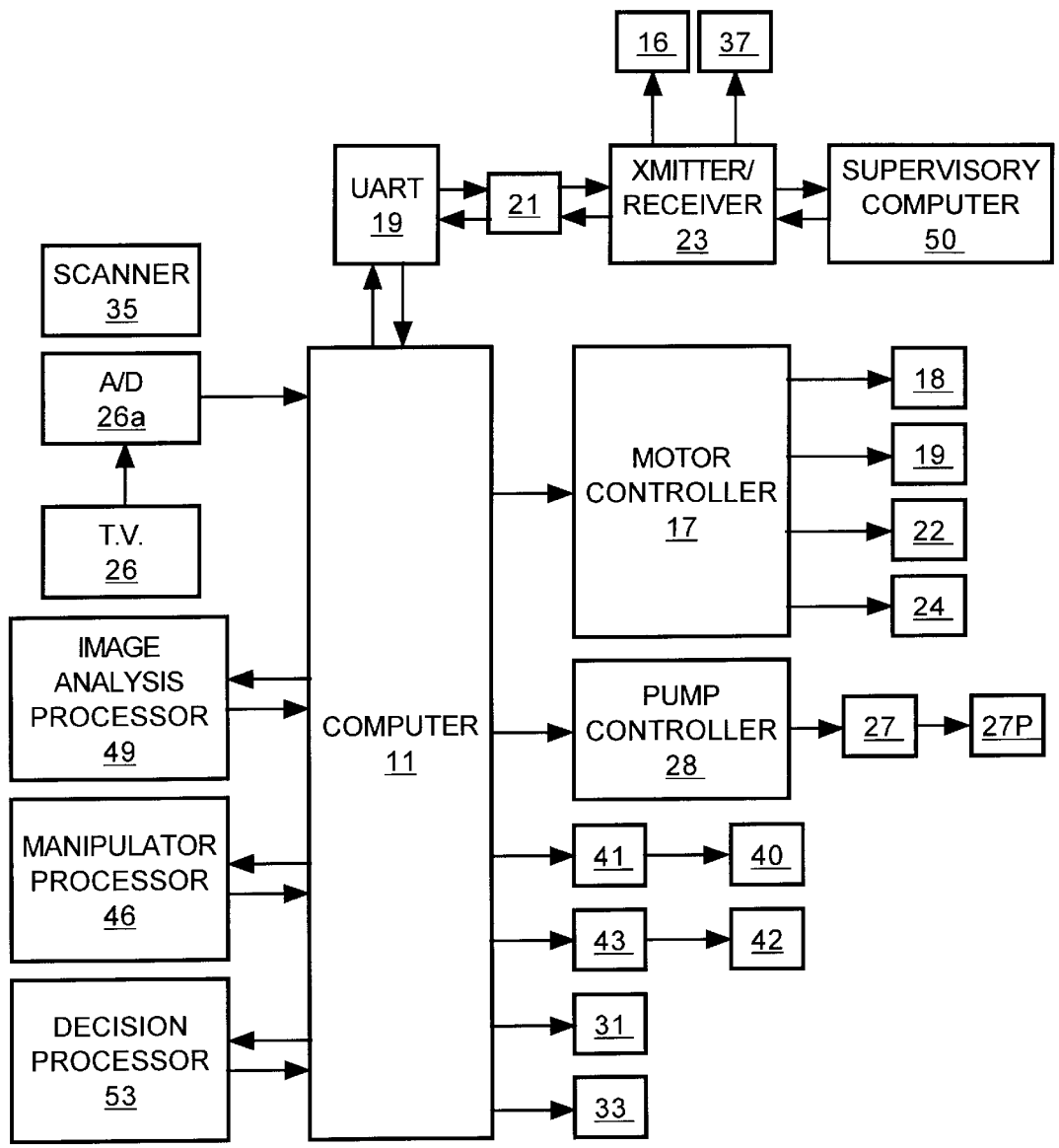
FIG. 7 is a block diagram of a computer system for controlling the operation of a manipulator apparatus.

In FIG. 7 is shown a block diagram of a system 10 for controlling the operation of the manipulator apparatus. A microprocessor or master computer 11 controls system operation and gates control and feedbacks signals between computers, sensors and motor controls. In one embodiment, the computer 11 may be located external to the rotor assembly and communicates with a terminal located within the rotor assembly via radio transmissions. In the embodiment described further herein, however, the entire system 10 including computer 11 is located onboard the rotor assembly and communicates with a supervisory computer located elsewhere via radio transmissions. Power for system 10 is supplied from an external source by the means shown in FIG. 6 and described above.

An automatic manipulator apparatus 15 in accordance with the invention, such as the embodiments illustrated in FIGS. 4 or 5, is automatically operated to perform one or more of the functions described above. Such functions include, for example, cleaning the inside surfaces of the walls of the tank of deposited chemicals or biological matter derived from one or more liquids stored or passed through the tank or taking part in or resulting from a reaction or reactions therein such as products of combustion, chemical and/or biological reactions. As detailed above, the manipulator is constructed with one or more laterally extending arms or arm assemblies operable to be power rotated about or with a vertically oriented rotor assembly. If the tank side wall is cylindrically shaped, such lateral arm is rotated about the longitudinal axis of the cylinder to carry an operating head on its end in circular scanning movement with respect to the inside surface of the cylindrical wall to permit a device on or defining the operating head to operate on or inspect all or select portions of the wall employing conventional inductive, capacitative, laser, x-ray, or ultrasonic scanning techniques as it scans or is held stationary at a select location when the computer 11 selectively stops movement of the head. As indicated, the operating head may support one or more liquid dispensing nozzles, stationary or power rotated brushes, scrapers, ultrasonic inspection or cleaning tools, cutting or grinding tools, suction cleaning heads, burners, drills, etc., all under control of computer 11.

FIG. 7 shows a computer 11 which is assumed for purposes of this description to be a microprocessor together with associated memory and I/O circuitry. Computer 11 communicates with various control and data collection elements located on the rotor assembly via a bidirectional bus (not shown). Communication with supervisory computer 50, located external to the rotor assembly, is effected by a UART 19 interfaced to the computer 11 and a modem 21 adapted to transmit and receive radio signals via transmitter/receiver 23. Separate radio links are used to establish communication between the computer 11 and other devices located external to the rotor assembly. Motor 16, for example, operates to power rotate the rotor assembly about the longitudinal axis of the tank (corresponding to motor 69 in FIG. 1 or motor 81 in FIG. 2) and is controlled by the computer 11 through radio transmitter 23. Similarly, a drain solenoid 37 is operated to open and close a drain valve (or drain pump) in response to control signals from 11 transmitted via radio transmitter 23.

Connected to receive control signals from computer 11 are operating head servo controllers 17 for driving operating head motors 18 and 20, a reversible manipulator gripper motor 22, and a tool motor 24. Motor 18 operates to drive such arm up and down in stepped increments, or at constant speed. Motor 20 and any additional operating head motors operate to power other parts or assemblies of the manipulator such as in pivoting the head or its tool axis, actuating a gripper, or driving one or more other arms or arm assemblies thereof to operably position the operating head with respect to the side and bottom walls of the tank or top wall thereof if the tank is closed.

A pump controller 28 operates a first pump motor 27 to drive a first pump 27P to pump one or more liquids such as water, steam, foam detergent or any other cleaning fluid at high velocity to clean residue or other deposits from the wall of the tank as the manipulator arm and a nozzle on the operating head rotate in parallel circular movements or spirally with respect to the cylindrical wall. Liquid pumps 40 and 42 are operated by control signals from respective controllers 41 and 43 which receive signals from computer 11. The two pumps may be controllably operated to pump additional cleaning or coating liquids to the operating head. A valve solenoid or motor 31 turned on and off or variably controlled by signals gated thereto from computer 11 may be employed to release or pump a coating fluid for coating or repairing select portions of the tank wall while a vacuum pump motor or solenoid 33 connected to a source of vacuum may selectively provide such vacuum cleaning or removing material from the wall or bottom of the tank or for picking up select objects or solid material from the bottom of the tank or surface of a liquid therein.

A scanning system for image recognition and control includes a television camera 26 mounted on or adjacent the operating head to scan surfaces and objects adjacent the head in order to control head movement and operation of the head tool or inspection device in accordance with the image information detected thereby and the operation of image analysis module 49 which receives and analyzes the image signals output by the camera. Video signals generated by camera 26 are digitized by an analog-to-digital converter and then fed to computer 11. The video signals may also be transmitted by computer 11 to the supervisory computer 50 via modem 21 for further analysis or display.

Also shown communicating with computer 11 are manipulator control processor 46, a decision processor 53, and an image analysis processor 49 which may be either dedicated hardware components or software modules running in memory. Fuzzy logic and neural network electronics may be employed in any or all of the processors 46, 49 and 53. The latter processor 53 may be employed to receive data code signals from the other computers and output control codes for controlling one or more of the described motors, solenoids, etc.

A scanning inspection device 35 operates to feed data to the computer 11, which scanning device may comprise one or more television cameras and/or other types of electro-optical, ultrasonic, MRI, x-ray and/or CAT scanners of contaminants on the walls of the tank and/or the internal structure of such wall(s). Such scanning device(s) or television camera may be mounted on or adjacent the operating head of the manipulator and the image or vision signals output thereby may be computer processed and analyzed. The computer 11 may be preprogrammed in its operation(s) to execute predetermined scanning and operating head functions and/or may be adaptively controlled to function in response to signals generated by one or more of the scanners described above.

Although the invention has been described in conjunction with the foregoing specific embodiments, many alternatives, variations, and modifications will be apparent to those of ordinary skill in the art. Those alternatives, variations, and modifications are intended to fall within the scope of the following appended claims.

What is claimed is:

1. A computer operated material processing apparatus comprising:
   a centrifuge tube for containing a liquid mixture and adapted for rotation about an axis by a mechanically driven rotor so as to subject the mixture to centrifugal forces;
   a scanning device for detecting the presence of specific test particles injected into the mixture and generating scanning signals in accordance therewith;
   an injector for injecting test particles into the mixture, said test particles being detectable by said scanning device and having a sedimentation constant approximately equal to a component of the mixture that is desired to be separated;
   a computer for analyzing the scanning signals and controlling the rotation of the centrifuge tube in accordance with the scanning signals so as to localize said specific particles in a desired sedimentation layer of said tube; and
   a reaction column comprising immobilized molecules with a specific binding affinity for said test particles for removing said test particles when said mixture is passed therethrough.

2. An apparatus in accordance with claim 1 wherein said computer is operable to control the duration for which said centrifuge tube is rotated.

3. An apparatus in accordance with claim 1 wherein said scanning device comprises a laser for irradiating specific particles in the mixture and a photodetector for detecting the light scattered thereby.

4. An apparatus in accordance with claim 1 wherein said scanning device comprises a laser for irradiating fluorescently labeled specific particles in the mixture and a photodetector for detecting the light scattered or emitted thereby.

5. An apparatus in accordance with claim 1 wherein said computer is operable to control the rate at which said centrifuge tube is rotated.

6. An apparatus in accordance with claim 1 further comprising:
   a mixing vessel for containing fluid components to be mixed;
   a fluid agitating device for imparting motion to the fluid components within said mixing vessel;
   a computer for controlling the operation of said agitating device;
   a scanning device for scanning the fluid components within the mixing vessel during mixing, generating scanning signals indicative of a quality of the mixing, and feeding said scanning signals to said computer.

7. An adaptively controlled centrifugal separator comprising:
   a housing into which may be flowed an input stream of a feedstock liquid whose components are desired to be separated, said housing containing an impeller for imparting rotation to the liquid contained therein and subject the fluid to centrifugal forces causing separation of components making up the liquid in accordance with density, said separated components making up a plurality of output streams;
   a scanning device for detecting the presence of specific test particles in a stream and generating scanning signals in accordance therewith;
   an injector for injecting test particles into the feedstock liquid, said test particles being detectable by said scanning device and having a sedimentation constant approximately equal to a component of the feedstock liquid whose concentration in a particular stream is desired to be controlled;
   a computer for analyzing the scanning signals, determining the concentration of particles in a particular stream, and controlling the rotation of the impeller so as to maintain a desired concentration of said specific particles in a particular stream; and
   a reactor column into which is flowed a particular stream, said reactor column containing immobilized molecules for removing said test particles by binding therewith.

8. A centrifugal separator in accordance with claim 6 further comprising a control valve for controlling the flow of liquid in a particular stream, said control valve being actuated under control of said computer in a manner so as to maintain a desired concentration of said specific particles in the particular stream.

* * * * *